United States Patent [19]
Coulter

[11] Patent Number: 5,417,666
[45] Date of Patent: May 23, 1995

[54] STERILE CATHETER SHIELD

[76] Inventor: Prince J. Coulter, 360 Championship Dr., Athens, Ga. 30607

[21] Appl. No.: 205,381
[22] Filed: Mar. 4, 1994
[51] Int. Cl.⁶ .............................................. A61M 5/00
[52] U.S. Cl. ...................................... 604/172; 604/349
[58] Field of Search ................... 604/49, 349, 171, 172

[56] References Cited

U.S. PATENT DOCUMENTS

| | | | |
|---|---|---|---|
| 1,878,671 | 9/1932 | Cantor. | |
| 3,344,791 | 10/1967 | Foderick | 128/349 |
| 3,421,509 | 1/1969 | Fiore | 128/349 |
| 3,683,928 | 8/1972 | Kuntz | 604/171 |
| 4,023,559 | 5/1977 | Gaskell | 128/2 W |
| 4,062,363 | 12/1977 | Bonner, Jr. | 604/171 |
| 4,652,259 | 3/1987 | O'Neil | 604/54 |
| 5,037,404 | 8/1991 | Gold et al. | 604/282 |

Primary Examiner—Jerome J. Kruter
Attorney, Agent, or Firm—S. Pal Asija; Larry Uland

[57] ABSTRACT

A method and apparatus is disclosed for catheterization of a urinary tract through an urethra containing infectious agents, which apparatus including a catheter tube disposed within a two-piece subassembly including a semi-rigid funnel member and a removable cover member, the combination serving to substantially reduce the incidence of infection upon the insertion of the catheter into the bladder.

4 Claims, 2 Drawing Sheets

STERILE CATHETER SHIELD

BACKGROUND OF THE INVENTION

1. Field Of The Invention

The present invention relates to improvements in medical instruments. More particularly, the present invention relates to an improved apparatus to catheterize a human urethra so as to avoid bacterial contamination resultant from such procedure and a method for its use.

2. Description Of The Prior Art

One of the most common medical procedures is the insertion of a medical instrument into a body passage, for example, the insertion of a catheter through the urethra into the bladder.

Despite significant advances in medical technology, however, this procedure continues to give rise to high incidence of infection in the upper urinary tract and bladder. This is because the urethra, and especially the male urethra, is unsterile for a certain portion of its length. In this connection, the National Center for Disease Control has determined that the first three inches of the male urethra is contaminated with various infectious agents, whereas the infectious area of the female urethra is only about one and one half inches.

It is standard practice for catheterization to be performed only after the area around the urethra has been thoroughly cleaned, the catheter has been sterilized and the operator has donned surgical gloves and mask. Despite this precaution, subsequent urinary tract infection is still commonplace. The reason for this has been identified as resulting from bacteria which are present within the urethra itself, particularly at its outer end. Such bacteria is difficult, if not impossible, to remove prior to insertion of the catheter.

The urethra is naturally provided with a defense mechanism to prevent the migration of bacteria into the upper urinary tract and ultimately the bladder. This defense mechanism has been described as a high pressure area located in the intermediate urinary tract, the presence of which defines a sterile area immediately below the bladder. As the catheter is introduced into urethra, however, it comes into contact with the bacteria residing in the contaminated lower zone and carries these agents along the urethra and into the bladder, thereby resulting in infection.

No amount of pre-cleaning of the area external of the urethra will generally prevent infection of the type described above which results from catheterization.

Several proposals have been made to prevent the catheter from carrying bacteria along the urinary tract, but none of these have proved entirely successful, resulting in the general failure of the apparatus and techniques associated with such proposals to achieve commercial success. For example, U.S. Pat. Nos. 3,332,424 (Minteer), 3,908,635 (Vick) and 3,908,663 (Vick) describe assemblies having a catheter tube of thin flexible material and a rigid collar secured around one end of the catheter tube. In use, these catheters are operated by placing the collar around the entrance to the body passage and pushing the tube through the collar so that the tube progressively everts along the passage. In this way movement of the tube wall relative to the passage wall is reduced so that bacteria are less likely to be carried along the passage.

Notwithstanding these designs, bacteria can nevertheless be forced into the leading open end of the catheter tube as it everts, and then be discharged and redeposited further up the passage on continued eversion of the tube. Therefore, while these previously proposed catheters represent an improvement over a basic catheter tube, they nevertheless cause a degree of contamination by carrying bacteria further up the urethral passage.

U.S. Pat No. 3,669,099 (Silverman) describes a similar system to the above-described prior art in that it discloses an everting tubing for contacting a body cavity wall. In the Silverman patent, however, the ends of the tubing are secured and sealed to a rigid cylindrical tube surrounding the tubing so that the tubing forms a closed toroidal chamber which is then filled with a fluid. A long cylindrical medical instrument can then be pushed through the tubing and the pressure of fluid causes the tubing to evert as the instrument passes through it.

The previously proposed arrangement is complex as a fluid inlet must be provided in the rigid tube for injection of fluid to an appropriate pressure, and the presence of the toroidal chamber makes the apparatus rather wide and therefore somewhat uncomfortable for the patient. It is also relatively expensive to manufacture.

Responsive to the above problems, urinary catheter designs have been proposed which incorporate an axial sheath through which is inserted a smaller diameter catheter. U.S. Pat. No. 3,421,509 (Fiore) and West German Offenlegungsschrift No. 24 56 980 both have a urethral catheter in which the catheter tube is slidable within an impervious-walled sheath having a closure member in the form of overlapping flaps at its distal end. The sheath also has an external shoulder for engaging the mouth of the urethra to limit the extent of insertion of the sheath into the urethra. In Fiore the shoulder is stated to be about 1.5 inches from the distal end of the sheath. U.S. Pat. No. 4,023,559 (Gaskell) also has a catheter tube slidable within an impervious-walled sheath which has a closure formation at its distal end through which the catheter tube can extend. In the Gaskell design, no limitation is provided on the sheath to determine its extent of penetration. A sheathed design is also described in U.S. Patent No. 4,652,259 as issued to O'Neil. The sheath proposed by O'Neil is inserted through the contaminated lower tract upward in the urinary tract to a previously non-contaminated zone. In this fashion, the O'Neil assembly was proposed to act like a bridge over the contaminated area.

Disadvantages with these designs, however, also arise in the movement of bacteria upward in the urinary tract upon insertion of the catheter assembly by contamination of the sheath during placement in the urethra. Notwithstanding the bridging effect of the sheath, it becomes contaminated during its passage through the infected area of the urethra and thus spreads these infectious agents to the catheter. Hence, these designs also provide for the opportunity of bacterial infection during the catheterization procedure.

SUMMARY OF THE INVENTION

The present invention addresses the above and other disadvantages of prior art urethral catheterization apparatus and techniques, without promoting the upward movement of infectious bacteria in the urinary tract.

The apparatus of the present invention is directed to an improved catheter sheath assembly comprising a cylindrical semi-rigid funnel member insertable into the urethra to a selected depth, and a removable flexible cover member in association with the funnel member such that the introduction of contamination onto selected portions of the funnel member which are contactible by an inserted catheter may be avoided as catheterization is completed. Upon insertion of the sheath assembly in the urethra, the cover member is removed so as to extract infectious agents which may have been introduced onto the cover member, and thereby keeping portions of the funnel member which were enwrapped by the cover member free of such infectious agents. Upon removal of the cover member, catheterization is completed by insertion of the catheter through the funnel member of the sheath assembly into the upper urinary tract and bladder so as to allow for the removal of liquid therefrom.

The present invention has a number of advantages over the art. One such advantage is the ability of the instant invention to reduce contamination occasioned by catheterization of the urinary tract. Another advantage is the two piece design of the catheter sheath which allows for ease and economy in construction.

These together with other objects of the invention, along with the various features of novelty which characterize the urinary catheter assembly of the instant invention, are pointed out with particularity in the claims appended hereto and forming a part of this disclosure. The more important objects of the instant invention have been outlined rather broadly in order that the detailed description thereof which follows may be better understood, and in order that the present contribution to the art may be better appreciated. For a better understanding of the invention, its operational advantages and the specific objects attained by its uses, reference should be made to the accompanying drawings and descriptive matter in which there are illustrated various embodiments of the invention.

Those skilled in the art will readily ascertain, however, that the instant invention is capable of other embodiments and of being practiced and carried out in various ways. In this respect, the details of construction disclosed herein, and the arrangements or relative dimensions of the components set forth in the following description and appended drawings are for illustrative purposes, only, and are not intended to be limiting in scope. Those skilled in the art will appreciate, as well, that the conception upon which this disclosure is based, may readily be utilized as a basis for the designing of other structures, methods and systems for carrying out the several purposes of the present invention. Said other structures may include, but not be limited to, those which are aesthetic in nature, or those which include the substitution of other materials as they become available, and which substantially perform the same function in substantially the same manner with substantially the same result as the present invention. It is important, therefore, that the claims appended hereto be regarded as including such equivalent structures, constructions, methods and systems insofar as these do not depart from the spirit and scope of the instant invention.

BRIEF DESCRIPTION OF THE DRAWINGS

The invention will be better understood and objects other than those set forth above will become apparent when consideration is given to the following detailed description. Such description makes reference to the appended drawings, wherein.

DETAILED DESCRIPTION OF THE PREFERRED EMBODIMENTS

A preferred embodiment of the present invention is illustrated by reference to Figures 1—4 and generally includes a sheath assembly 2 through which a conventional catheter 12 of appropriate outer diametrical dimensions is introduced into the bladder (not shown), past the contaminated zone 13 in the urethra 11.

Figure 1:
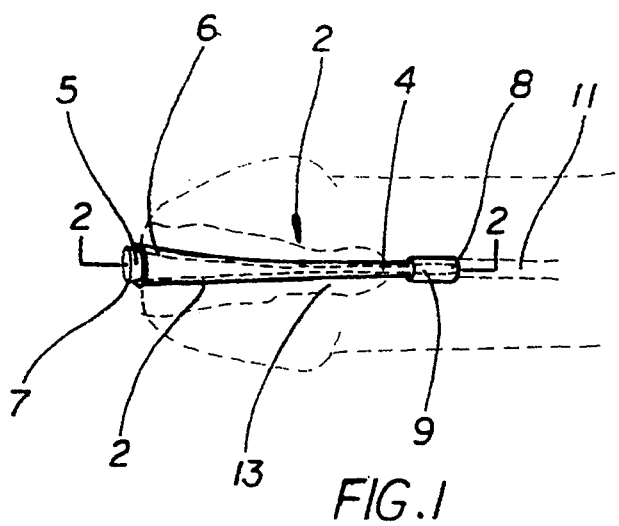
FIG. 1 illustrates a side view of the sheath assembly, including a semi-rigid funnel member and a flexible cover member, positioned in the urethra prior to removal of the cover member.

Figure 1 illustrates a sheath assembly 2 which comprises a semi-rigid funnel member 4 and a flexible cover member 5. Funnel member 4 defines a proximal end 6, a distal end 8 and a hollow bore 10. In a preferred embodiment, funnel member 4 may be provided with a fluted, larger diameter proximal end 6 to aid in the insertion of the catheter 12 as will be described below. Funnel member 4 also preferably defines a tapered distal end 8 to aid in insertion into the urethra 11. To also aid in insertion, it is desirable to coat the exterior of funnel member 4 with silicone or other similar lubricant.

It is contemplated that the funnel member 4 may be constructed of a flexible plastic, polyethylene or other similar material. In this connection, the choice of materials used in funnel member 4 will largely dictate the wall thickness used in its construction.

Figures 2, 3:
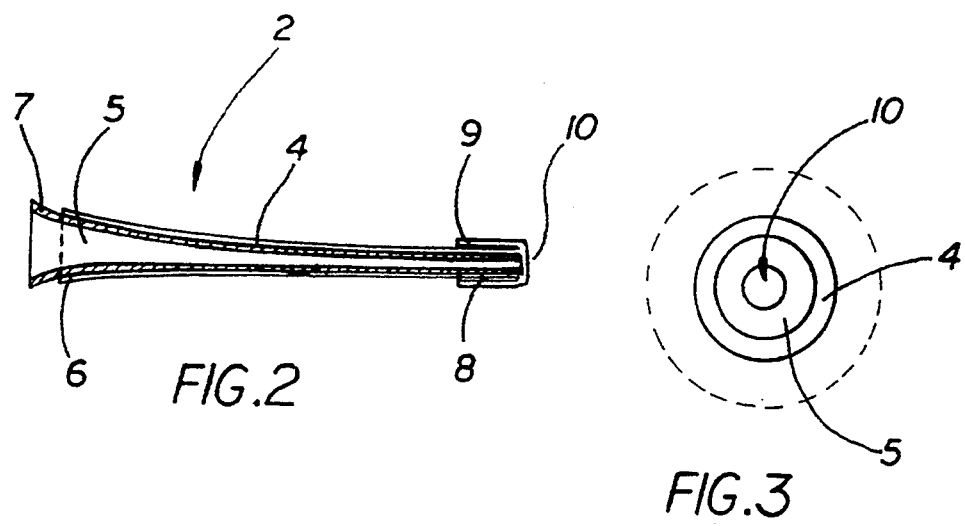
FIG. 2 illustrates a section view of the sheath assembly illustrated in FIG. 1, along lines 2—2.
FIG. 3 illustrates an end view of the sheath assembly illustrated in FIG. 1.
Figure 4:
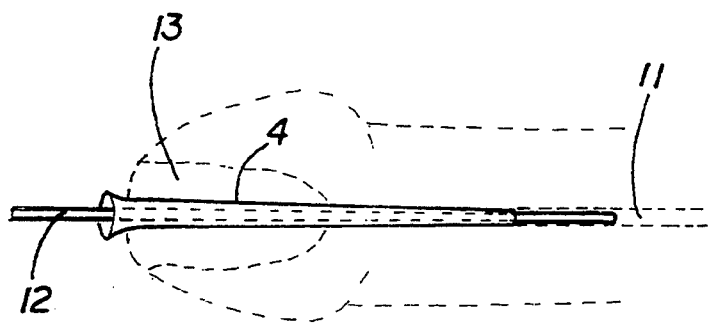
FIG. 4 illustrates a side view of the funnel member positioned in the urethra and receivable to the catheter.

By reference to FIGS. 1-3, cover member 5 defines a proximal end 7 and distal end 9 and is designed to be axially disposed in funnel member 4 in a contacting relation. In a preferred embodiment, cover member 5 defines an outer diameter closely matching the inner diameter of funnel member 4 so as to provide for a close tolerance fit therebetween.

In a preferred embodiment, cover member 5 is formed to a greater axial length than funnel member 4 such that, upon assembly, a selected length of cover member 5 extends from both ends of funnel member 4 so as to define extensions or overlaps. This extension or overlap of cover member 5 vis-a-vis funnel member 4 is desirable for at least two reasons. First, the overlap of the distal end 9 of cover member 5 protects the inner diameter and exterior surfaces of the distal end 8 of the funnel member 4 from the introduction of infectious agents present in the urinary tract during insertion of the funnel member 4. The proximal extension of cover member 5 also defines means to remove cover member 5 once the funnel member 4 is properly positioned in the urethra 11.

In a preferred embodiment, cover member 5 is temporarily secured to funnel member 4 via a light film of a lubricating medium, such as beeswax, glycerin, anhydrous lanolin, lanolin alcohol, mineral oil, paraffin, petrolatum, petroleum jelly, shark liver oil, thyme oil, or the like, which lubricating medium is between the interior surface of the funnel member 4 and the exterior surface of the cover member 5 and also desirably covers the interior surface of the portion of the cover member 5 protruding from and enwrapping the distal end 8 which is in contact with the urethra, for ease in extraction. It is also desirable that such lubricating medium contain a suitable bactericide, such as polymyxin B sulfate, bacitracin zinc, neomycin, and lidocaine, or the like, for inhibiting the growth of infectious bacteria in the proximity of the inserted funnel member 4.

Once cover member 5 has been removed, the catheter 12 is inserted through the bore 10 defined in funnel member 4 for insertion through the urethra into the bladder so as to allow for the extraction of fluid therefrom.

The method of catheterization of the human urethra utilizing the embodiment of the present invention comprising assembly 2 may be described as follows. The distal end of assembly 2 is inserted in the urethra 11 to a depth greater than the extent of contamination 13 such that the distal end of assembly 2 extends beyond said contaminated area 13 and the proximal end thereof remains outside the entrance to the urethra 11 for control and ease of extraction. In the male urethra, this insertion depth will generally be greater than three inches. In the female urethra, this depth will generally be greater than a length of from one to one-and-one-half inches. Once assembly 2 is secured in the urethra, cover member 5 is removed by grasping the length of the proximal end 7 protruding beyond the fluted proximal end 6 of funnel member 4 and pulling thereon. Removal of cover member 5 results in the removal of contaminants that may have collected in the bore 10 of assembly 2 or on the distal end 9 of the cover member 5 during insertion. In this embodiment of the instant invention, the portion of the distal end 9 of the cover member 5 which is contaminated during insertion into the urethra 11, is caused to collapse upon itself during extraction of the cover member 5, thereby entrapping any contamination thereon within the bore of the cover member 5. Catheter 12 is then inserted through member 4 into the urethra 11 via the fluted proximal end 6, for introduction to the bladder whereupon fluid may then be extracted from the bladder.

An alternate embodiment of the present invention is illustrated by reference to FIGS. 5–7 and generally includes a sheath assembly 3 through which a conventional catheter of appropriate outer diametrical dimensions is introduced into the bladder (not shown), past the contaminated zone 13 in the urethra 11.

Figure 5:
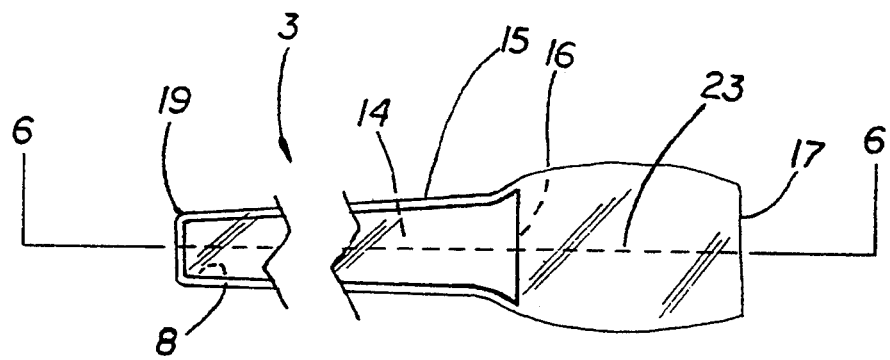
FIG. 5 illustrates a broken side view of an alternate embodiment of the sheath assembly including a semi-rigid funnel member and a flexible cover member.

FIG. 5 illustrates a sheath assembly 3 which comprises a semi-rigid funnel member 14 and a flexible cover member 15. Funnel member 14 is substantial similar to the funnel member 4 of the embodiment of the present invention illustrated in FIGS. 1–3, defining a proximal end 16, a distal end 18 and a hollow bore 20. It is preferable that funnel member 14 is provided with a fluted, larger diameter proximal end 16 to aid in the insertion of the catheter 12 as will be described below. Funnel member 14 also preferably defines a tapered distal end 18 to aid in insertion into the urethra 11.

Figure 6:
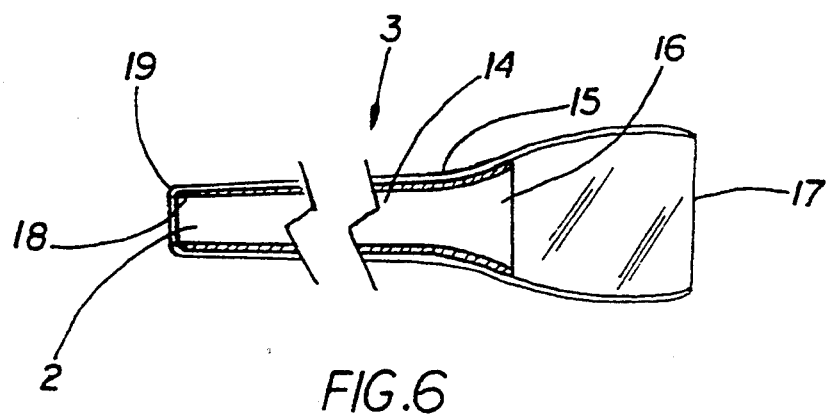
FIG. 6 illustrates a section view of the embodiment of the sheath assembly illustrated in FIG. 5, along lines 6—6.
Figure 7:
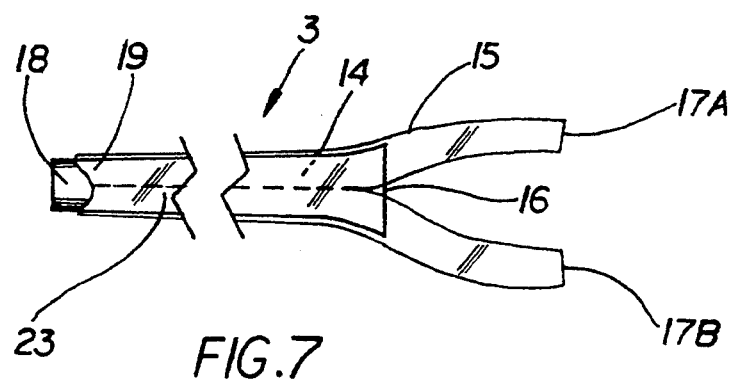
FIG. 7 illustrates a side view of the embodiment of the sheath assembly illustrated in FIG. 5 in which the flexible cover member has been partially removed from the semi-rigid funnel member.

By reference to FIGS. 5–7, cover member 15 defines a proximal end 17 and distal end 19 and is designed to be axially disposed outside the funnel member 14 in a contacting relation, such that the entire funnel member 14 is overlapped by the cover member 15 during insertion of the assembly 3 into the urethra 11. In a preferred embodiment, the cover member 15 defines an inner diameter closely matching the outer diameter of funnel member 14 so as to provide for a close tolerance fit therebetween. To aid in insertion of the assembly member 3 into the urethra, it is desirable to coat the exterior of the cover member 15 with a suitable lubricant such as silicone. To also aid in subsequent extraction of the funnel member 14, it is desirable to coat the exterior of the funnel member 14 with silicone or other similar lubricant.

It is contemplated that the funnel member 14 may be constructed of a flexible plastic, polyethylene or other similar material. In this connection, the choice of materials used in funnel member 4 will largely dictate the wall thickness used in its construction. It is further contemplated that the cover member be composed of a flexible film, such as polyethylene terephthalate or the like.

In a preferred embodiment, cover member 15 is formed to a greater axial length than funnel member 14 such that, upon assembly, a selected length of cover member 15 extends from the proximal end of funnel member 14 so as to define a graspable extension. The proximal extension of cover member 15 defines means to remove cover member 15 once the funnel member 14 is properly positioned in the urethra 11. To aid further in the extraction of the cover member 15 from the funnel member 14, it may be desirable to provide a semi-perforation line 23 on the cover member 15 defining a central plane through the axis of the assembly 3. With this, the distal end 19 of the cover member 15 may be more readily perforated by the distal end 18 of the funnel member 14, for slidable removal therefrom via grasping the proximal end 17 of the cover member 15 and separating said end 17 into two portions 17A and 17B and pulling thereon.

In a preferred embodiment, cover member 15 is temporarily secured to funnel member 14 via a light film of a lubricating medium, such as beeswax, glycerin, anhydrous lanolin, lanolin alcohol, mineral oil, paraffin, petrolatum, petroleum jelly, shark liver oil, thyme oil, or the like, which lubricating medium is between the exterior surface of the funnel member 14 and the interior surface of the cover member 15. It is also desirable that such lubricating medium contain a suitable bactericide, such as polymyxin B sulfate, bacitracin zinc, neomycin, and lidocaine, or the like, for inhibiting the growth of infectious bacteria in the proximity of the inserted funnel member.

Once cover member 15 has been removed, the catheter 12 is inserted through the bore 20 defined in funnel member 14 for insertion through the urethra into the bladder so as to allow for the extraction of fluid therefrom.

The method of catheterization of the human urethra utilizing the embodiment of the present invention comprising assembly 3 may be described as follows. The distal end of assembly 3 is inserted in the urethra 11 to a depth greater than the extent of contamination 13 such that the distal end of assembly 3 extends beyond said contaminated area 13 and the proximal end thereof remains outside the entrance to the urethra 11 for control and ease of extraction. Once assembly 3 is secured in the urethra, cover member 15 is removed by grasping the length of the proximal end 17 protruding beyond the fluted proximal end 16 of funnel member 14 and pulling thereon, preferably dividing the proximal end 17 of the cover member 15 into a pair of ends 17A and 17B for use in further dividing the cover member 15 in two, along said semi-perforation line 23. Removal of cover member 15 results in the removal of contaminants that may have collected on the exterior surface of the assembly 3 during insertion. Catheter 12 is then inserted through member 14 into the urethra 11 via the fluted proximal end 16, for introduction to the bladder whereupon fluid may then be extracted from the bladder.

DEFINITIONS

While every attempt has been made to avoid the use of terms of art, and to use the conventional dictionary meaning of terms, the following definitions are included here for clarification:

Semi-rigid=a condition roughly halfway between flexible and rigid. In this context semi-rigid and semi-flexible are synonyms.

The inventor has given a non-limiting description of two embodiments of the present invention, to which many changes may be made without deviating from the spirit of the invention. While this invention has been described with reference to these illustrative embodiments, this description is not intended to be construed in a limiting sense. Various modifications and combinations of the various embodiments as well as other embodiments of this invention will be apparent to a person skilled in the art upon reference to this description. It is therefore contemplated that the appended claims cover any such modifications and/or embodiments that fall within the true scope of the present invention. Further benefits and advantages of the present invention will become obvious to those skilled in the art in light of the following claims:

What is claimed is:

1. A sheath assembly for use with a urinary catheter, comprising:
   a sheath assembly
   a cylindrical semi-rigid funnel member having a proximal end and a distal end, and a removable cover member disposed in an axial relation to the funnel member such that upon placement of said sheath assembly into a urethra said cover member may be removed preliminary to the introduction of the catheter there through, thereby substantially reducing the incidence of infection resultant from placement of said sheath assembly into a urethra wherein said cover member is removably coupled to said funnel member via a lubricating agent.

2. A urinary catheter assembly for use in removing fluid from a human bladder without promoting infection, said assembly comprising:
   a sheath subassembly having proximal and distal ends and comprising a cylindrical semi-rigid funnel member and a cover member removably coupled in an axial relation, wherein said cover member has a length greater than said funnel member and said funnel member describes a fluted proximal end, a tapered distal end and a hollow bore therethrough, and a catheter axially receivable in the bore defined in said funnel member for introduction into the bladder and wherein said cover member is secured to said funnel member via a lubricant.

3. A urinary catheter shield assembly for use in removing fluid from a human bladder without promoting infection, said assembly comprising:
   a sheath subassembly having proximal and distal ends and comprising a cylindrical semi-rigid funnel member and a cover member removably coupled in an axial relation, wherein said cover member has a length greater than said funnel member and said funnel member describes a fluted proximal end, a tapered distal end and a hollow bore therethrough, and a catheter axially receivable in the bore defined in said funnel member for introduction into the bladder and wherein the outer diameter of said funnel member is provided with a lubricating medium preliminary to introduction into a urethra.

4. A urinary catheter assembly for use in removing fluid from a human bladder without promoting infection, said assembly comprising:
   a sheath subassembly having proximal and distal ends and comprising a cylindrical semi-rigid funnel member and a cover member removably coupled in an axial relation, wherein said cover member has a length greater than said funnel member and said funnel member describes a fluted proximal end, a tapered distal end and a hollow bore therethrough, and a catheter axially receivable in the bore defined in said funnel member for introduction into the bladder and wherein said cover member is provided with a means to extract it from the urethra after insertion of the sheath subassembly into the urethra.

* * * * *